United States Patent
Levy et al.

(10) Patent No.: US 10,058,419 B2
(45) Date of Patent: Aug. 28, 2018

(54) OXIDATION RESISTANT BIOPROSTHETIC TISSUES AND PREPARATION THEREOF

(75) Inventors: Robert J. Levy, Merion Station, PA (US); Ivan Alferiev, Clementon, NJ (US); Stanley Stachelek, Philadelphia, PA (US); Jeanne M. Connolly, Philadelphia, PA (US); Abigail Christian, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 687 days.

(21) Appl. No.: 14/232,005

(22) PCT Filed: Jul. 11, 2012

(86) PCT No.: PCT/US2012/046226
§ 371 (c)(1),
(2), (4) Date: Jun. 4, 2014

(87) PCT Pub. No.: WO2013/009851
PCT Pub. Date: Jan. 17, 2013

(65) Prior Publication Data
US 2014/0288641 A1      Sep. 25, 2014

Related U.S. Application Data

(60) Provisional application No. 61/506,400, filed on Jul. 11, 2011.

(51) Int. Cl.
*A61L 27/36* (2006.01)
*A61F 2/24* (2006.01)
(Continued)

(52) U.S. Cl.
CPC ............ *A61F 2/2412* (2013.01); *A61K 35/12* (2013.01); *A61L 27/3604* (2013.01);
(Continued)

(58) Field of Classification Search
CPC ........ A61F 2/24; A61F 2/2418; A61F 2/2439; A61F 2250/0039; A61F 2/2412;
(Continued)

(56) References Cited

U.S. PATENT DOCUMENTS 4,115,590 A * 9/1978 Lerner .................. A61K 31/05
514/712
4,481,009 A * 11/1984 Nashef ................ A61L 27/3687
623/2.42
(Continued)

FOREIGN PATENT DOCUMENTS

CN          101224313        7/2008

OTHER PUBLICATIONS

Antioxidants, Encyclopedia of Polymer Science and Technology, vol. 5, pp. 164-197, Copyright John Wiley & Sons, Inc.
(Continued)

*Primary Examiner* — Seema Mathew
(74) *Attorney, Agent, or Firm* — RatnerPrestia

(57) ABSTRACT

Oxidation resistant bioprosthetic tissues and oxidation resistant bioprosthetic heart valve leaflets are described. Also provided are methods for preparing the oxidation resistant bioprosthetic tissues and bioprosthetic heart valve leaflets, and methods for preventing oxidative degeneration in bioprosthetic tissues, including immobilizing covalently an effective amount of an antioxidant to the bioprosthetic tissue.

28 Claims, 6 Drawing Sheets

(51) Int. Cl.
  *A61L 27/50* (2006.01)
  *A61K 35/12* (2015.01)
(52) U.S. Cl.
  CPC ......... *A61L 27/3687* (2013.01); *A61L 27/505* (2013.01); *F04C 2270/041* (2013.01)
(58) Field of Classification Search
  CPC ........ A61L 27/507; A61L 29/08; A61L 29/12; A61L 27/3604; A61L 27/3625; A61L 27/50; A61L 27/505
  See application file for complete search history.

(56) References Cited

U.S. PATENT DOCUMENTS

| | | | |
|---|---|---|---|
| 5,447,536 | A | 9/1995 | Girardot et al. |
| 5,562,922 | A | 10/1996 | Lambert |
| 5,612,321 | A * | 3/1997 | Nguyen ................. A61K 8/735 424/401 |
| 5,733,339 | A | 3/1998 | Girardot et al. |
| 5,770,609 | A * | 6/1998 | Grainger .............. A61K 9/0024 514/319 |
| 6,121,041 | A * | 9/2000 | Mirsch, II .......... A61L 27/3687 435/265 |
| 6,132,473 | A | 10/2000 | Williams et al. |
| 6,506,339 | B1 | 1/2003 | Girardot et al. |
| 7,479,164 | B2 | 1/2009 | Girardot et al. |
| 7,579,381 | B2 | 8/2009 | Dove |
| 7,635,734 | B2 | 12/2009 | Alferiev et al. |
| 7,972,376 | B1 | 7/2011 | Dove et al. |
| 8,038,927 | B2 | 10/2011 | Muratoglu et al. |
| 8,808,726 | B2 * | 8/2014 | Atanasoska ........... A61L 31/148 424/426 |
| 9,320,830 | B2 * | 4/2016 | Dove ................ A61L 27/3604 |
| 9,731,047 | B2 * | 8/2017 | Oral ........................ A61L 27/50 |
| 2001/0023372 | A1 * | 9/2001 | Chen ........................ A01N 1/00 623/23.72 |
| 2006/0063894 | A1 * | 3/2006 | Alferiev ................. C08G 18/83 525/452 |
| 2007/0254005 | A1 * | 11/2007 | Pathak .................... A61K 35/12 424/423 |
| 2007/0264306 | A1 * | 11/2007 | Flameng ............. A61L 27/3625 424/423 |
| 2008/0177381 | A1 | 7/2008 | Navia et al. |
| 2009/0164005 | A1 * | 6/2009 | Dove ................... A61L 27/3604 623/2.13 |
| 2010/0004333 | A1 * | 1/2010 | Stocker ................. C07C 323/20 514/548 |
| 2010/0210015 | A1 * | 8/2010 | Alferiev ............... A61K 31/765 435/375 |
| 2011/0109017 | A1 * | 5/2011 | Muratoglu ............... A61L 27/16 264/488 |
| 2011/0165675 | A1 | 7/2011 | Dove et al. |
| 2012/0123557 | A1 * | 5/2012 | Carpentier ............. A61F 2/2415 623/23.72 |
| 2014/0005293 | A1 * | 1/2014 | Thomas ................... A61L 27/16 522/75 |
| 2014/0288641 | A1 * | 9/2014 | Levy ....................... A61K 35/12 623/2.13 |
| 2017/0066905 | A1 * | 3/2017 | Hoelzl .................... C08K 5/523 |

OTHER PUBLICATIONS

Briand et al., "Metabolic Syndrome Is Associated With Faster Degeneration of Bioprosthetic Valves," American Heart Association, pp. 512-517, May 26, 2011, 7272 Greenville Avenue, Dallas, TX 72514.
Dyubchenko et al., "Synthesis and Hepatoprotector Activity of Water-Soluble Derivatives of Aminoalkylphenols," Pharmaceutical Chemistry Journal, vol. 40, No. 5, pp. 243-247, May 2006.
Ferrans et al.,"Structural Changes in Glutaraldehyde-Treated Porcine Heterografts Used as Substitute Cardiac Valves," Jun. 1979 The American Journal of Cardiology vol. 41, 1159-1184.
Fishbein et al., "Local Delivery of Gene Vectors From Bare-Metal Stents by Use of a Biodegradable Synthetic Complex Inhibits In-Stent Restenosis in Rat Carotid Arteries," Circulation. Apr. 22, 2008; 117(16): 2096-2103. doi:10.1161/CIRCULATIONAHA.107. 746412.
Ford et al., "Prevalence of the Metabolic Syndrome Among US Adults," JAMA, Jan. 16, 2002 vol. 287, No. 3, 356-359.
Greg T. Hermanson, Bioconjugate Techniques, Pierce Biotechnology, Thermo Fisher Scientific, Rockford, IL, USA, 2008, pp. 169-182, 182-192, 192-195, 204-210, 211-212, 507-545, 680-690, 690-697.
Schoen et al., "Calcification of Tissue Heart Valve Substitutes: Progress Toward Understanding and Prevention", Ann Thorac Surg, 2005, 79:1072-80.
Stachelek et al., "Prevention of oxidative degradation of polyurethane by covalent attachment of di-tert-butylphenol residues," Journal of Biomedical Materials Research Part A, 2006, pp. 653-661.
Stachelek et al., "Biological stability of polyurethane modified with covalent attachment of di-tert-butyl-phenol," Journal of Biomedical Materials Research Part A, 2007, pp. 1004-1011.
Stachelek et al., "Prevention of Polyurethane Oxidative Degradation With Phenolic-Antioxidants Covalently Attached to the Hard Segments: Structure Function Relationships", J Biomed Mater Res A. Sep. 1, 2010; vol. 94, No. 3, pp. 751-759.
Wilchek et al., "Introduction to Avidin-Biotin Technology, Methods in Enzymology," vol. 184, 1990, pp. 5-13.
Yeghiazaryan et al., "Prediction of Degeneration of Native and Bioprosthetic Aortic Valves: Issue-Related Particularities of Diabetes Mellitus," Infectious Disorders—Drug Targets 2008, 8, 88-99.
Zhai, et al., "Quercetin-crosslinked porcine heart valve m atrix: Mechanical properties, stability, anticalcification and cytocompatibility", Acta Biomaterialia, Aug. 3, 2009, vol. 6, pp. 389-395.
International Preliminary Report on Patentability and Written Opinion for International Appln. No. PCT/US2012/046226 dated Jan. 14, 2014.
International Search Report for International Appln. No. PCT/US2012/046226 dated Jan. 23, 2013.
Extended European Search Report for EP 12 81 1631 dated Mar. 9, 2015.
Alferiev I S et al: "A Novel Mercapto-Bisphosphonate as an Efficient Anticalcification Agent for Bioprosthetic Tissue S"; Journal of Organometallic Chemistry, Elsevier-Sequoia S.A. Lausanne, CH, vol. 690, No. 10, May 16, 2005 (May 16, 2005) , pp. 2543-2547, XP027708594,; ISSN: 0022-328X [Retrieved on May 16, 2005]; p. 2545.
Webb C L et al: "Inhibition of Bi0pr0sthetic Heart Valve Calcification With Aminodiph0sph0nate C0valently Bound to Residual Aldehyde Groups", Annals of Thoracic Surgery, New York, NY. US, vol. 46, No. 3,Sep. 1, 1988 (Sep. 1, 1988), pp. 309-316, XP000874363, p. 309-p. 310.
Zhai W et al: "Quercetin-Crosslinked Porcine Heart Valve Matrix: Mechanical Properties, Stability, Anticalcification and Cytocompatibility", Acta Biomaterialia, Elsevier, Amsterdam, NL, vol. 6, No. 2, Feb. 1, 2010 (Feb. 1, 2010), pp. 389-395, XP026811129, ISSN: 1742-7061 [Retrieved on Aug. 3, 2009] p. 389.
Stanley J. Stachelek et al: "Prevention of Polyurethane Oxidative Degradation With Phenolic Antioxidants Covalently Attached to the Hard Segments: Structure-Function Relationships", Journal of Biomedical Materials Research Part A, vol. 9999A, No. 3, Jan. 1, 2010 (Jan. 1, 2010), pp. NA-NA, XP055142535, ISSN: 1549-3296, DOI: 10.1002/JBM.A.32755.
Dombrecht E J et al: "Selective In Vitro Antioxidant Properties of Bisphosphonates", Biochemical and Biophysical Research Communications, Academic Press Inc. Orlando, FL, US, vol. 314, No. 3, Feb. 13, 2004 (Feb. 13, 2004), pp. 675-680, XP004485019, ISSN: 0006-291X, DOI: 10.1016/J.BBRC.2003.12.149.
Australian Examination Report for Australian Application No. 2012282660, dated Jul. 14, 2016, 3 pages.
Second Australian Examination Report for Australian Application No. 2012282660, dated Mar. 2, 2017, 4 pages.
European Communication for European Application No. 12811631. 6, dated Feb. 1, 2017, 6 pages.

(56) References Cited

OTHER PUBLICATIONS

European Commication for European Application No. 12 811 631.6, dated Oct. 27, 2017, 6 pages.

* cited by examiner

RAT SUBDERMAL EXPLANTS

A. CALCIFIED

B. NON-CALCIFIED

SHEEP BIOPROSTHETIC MITRAL VALVE EXPLANT

C. CALCIFIED

OXIDATION RESISTANT BIOPROSTHETIC TISSUES AND PREPARATION THEREOF

FIELD OF THE INVENTION

The invention relates generally to oxidation resistant bioprosthetic tissues and preparation thereof. In particular, the invention relates to bioprosthetic tissues treated with an anti-oxidant to prevent oxidative degeneration of the bioprosthetic tissues.

BACKGROUND OF THE INVENTION

Bioprosthetic heart valves are now used in an estimated 200,000 patients annually world wide. They generally fail over time due to heterograft leaflet malfunction. In about 80% of cases, bioprosthetic leaflet calcification is the cause of failure, and there has been an extensive amount of research related to this failure mechanism. The remaining 20% of these bioprostheses fail without evidence of calcification. Efforts have been made to prevent degeneration of bioprosthetic heart valves by mitigating calcification.

Oxidative stress occurs in living organisms due to an inflammatory cell response that gives rise to reactive oxygen species (ROS), and these can include nitric oxide, peroxynitrite, hydrogen peroxide, and superoxides. ROS can modify proteins and other macromolecules with either loss of function or structural damage. Living cells maintain an anti-oxidant system involving chiefly intracellular glutathione, and a variety of enzymes that can break down ROS. These ROS-enzymes include superoxide dismutase, catalase, glutathione reductase and others.

It has been reported that hypertension and metabolic disorders are two common risk factors for degenerative aortic valve disease (DAVD) (Yehgiazaryan et al. *Infectious Disorders—Drug Targets* 2008; 8:88-99). Metabolic syndrome (MS) has been found associated independently with accelerated degeneration of bioprosthetic valves (Briand et al. *Circulation* 2006; 114:I-512-7). However, whether oxidative stress is a contributing cause of the material failure of bioprosthetic heart valves has not been studied. Nor has the possibility of using anti-oxidants for preventing bioprosthetic heart valve leaflet deterioration been considered or reported.

Therefore, there remains a need for an effective treatment for preventing degeneration of bioprosthetic tissues in a subject.

SUMMARY OF THE INVENTION

The present invention is based on the realization that certain bioprosthetic tissue, such as a glutaraldehyde fixed heterograft tissue, contains neither viable cells nor ROS-scavenging enzymes, and thus is uniquely susceptible to oxidative attack. The applicant proposes to treat bioprosthetic tissue with an anti-oxidant to prevent oxidative degeneration of the bioprosthetic tissues.

In a first aspect of the invention, a bioprosthetic tissue treated with an effective amount of an antioxidant to prevent oxidative degeneration of the bioprosthetic tissue in a subject is provided. The bioprosthetic tissue may for example be in the form of a bioprosthetic heart valve leaflet. The antioxidant is covalently immobilized to the bioprosthetic tissue. The bioprosthetic tissue is treated with an effective amount of an antioxidant to prevent oxidative degeneration of the bioprosthetic tissue in a subject, such that the antioxidant is covalently immobilized to the bioprosthetic tissue.

The bioprosthetic tissue may be a heterograft or a homograft. The bioprosthetic tissue may be a bovine, ovine, porcine, equine, human tissue, or other vertebrate derived tissue. The bioprosthetic tissue may also be a heart, heart valve, pericardium, vascular graft, urinary tract, bladder component, tendon, bowel, or soft tissues. For example, the bioprosthetic tissue may be a heart valve tissue, preferably a porcine aortic valve or bovine pericardium. The bioprosthetic tissue may be fixed with glutaraldehyde, with epoxy-compounds (e.g., triglycidylamine), or other uncommonly used crosslinkers such as photo-fixation, or microwave fixation. Alternatively, the bioprosthetic tissue may be cryo-preserved with liquid nitrogen.

The antioxidant may be derived from a natural antioxidant, for example glutathione, ascorbic acid (vitamin C), lipoic acid, uric acid, carotenes, α-tocopherol (vitamin E), ubiquinol (coenzyme Q) and melatonin. Suitable coupling to the bioprosthetic tissue may be effected by linkers that react with carboxyls (e.g., carbodiimide), thiol reactive cross-linkers (such as described in Fishbein, I., Alferiev, I., Bakay, M., Stachelek, S. J., Sobolewski, P., Lai, M., Choi, H., Chen, I. W., and Levy, R. J., *Local delivery of gene vectors from bare-metal stents by use of a biodegradable synthetic complex inhibits in-stent restenosis in rat carotid arteries*, Circulation (2008) 117, 2096-2103), or via amino-reactive linking using succinimide-related agents, for example as shown in Scheme 4. Additional methods of attaching natural antioxidants such as those listed above to the bioprosthetic tissue may include use of substituted benzophenone-based photochemical linking techniques, for example as described in U.S. Pat. No. 7,635,734. Additionally, ascorbic acid may be attached using "click chemistry" or Staudinger ligation, using methods known in the art. Melatonin may for example be attached by appropriate substitution of the methyl group on the acetyl residue. Additional details regarding suitable techniques (reactions with carboxy and amino groups, photo-binding, chemistry of thiols and thiol-reactive groups, "click chemistry", Staudinger ligation, avidin-biotin binding, etc.) are described by Greg T. Hermanson, *Bioconjugate Techniques*, $2^{nd}$ Edition, Elsevier Inc., 2008. Binding of glutathione via the thiol group to the bioprosthetic tissue may also be used, resulting in formation of a dialkyl sulfide that may provide activity as a thiosynergist (discussed below). Suitable techniques for such binding are described, for example, by Fishbein et al., mentioned above.

The antioxidant may also be a synthetic antioxidant, for example, a phenol-based antioxidant. Preferably, the antioxidant is 4-substituted 2,6-di-tert-butylphenol (DBP) or a derivative thereof. More preferably, the antioxidant is 4-hydroxy-3,5-di-tert-butylphenolpropylamine hydrochloride (DBP-amine.HCl). The antioxidant may also be a combination of two or more antioxidant compounds.

Also provided is a method for preparing a bioprosthetic tissue of the present invention. The method comprises immobilizing covalently an effective amount of an antioxidant to the bioprosthetic tissue to prevent oxidative degeneration of the bioprosthetic tissue in a subject.

Also provided are compositions for preventing oxidative degeneration of a bioprosthetic tissue in a subject. The compositions comprise an antioxidant or combination of two or more antioxidants capable of being covalently immobilized to the bioprosthetic tissue. Suitable exemplary compositions according to the invention include tissue-reactive antioxidant constructs 7, 8 and 9 as shown in Scheme 3.

Also provided is a method for preventing oxidative degeneration of a bioprosthetic tissue in a subject is provided. The method comprises immobilizing covalently an effective amount of one or more antioxidant(s) to the bioprosthetic tissue.

Also provided is a method of treating a subject in need of a bioprosthesis, in which the bioprosthesis has immobilized to it one or more antioxidants as described above and elsewhere herein.

The subject may be a human, female or male. The subject may have suffered from the metabolic syndrome, hormonal deregulation, hypertension, extreme stress, or weight loss. The subject may have suffered from increased reactive oxygen species (ROS), or hyperglycemia-induced oxidative stress.

DETAILED DESCRIPTION OF THE INVENTION

Figure 1:
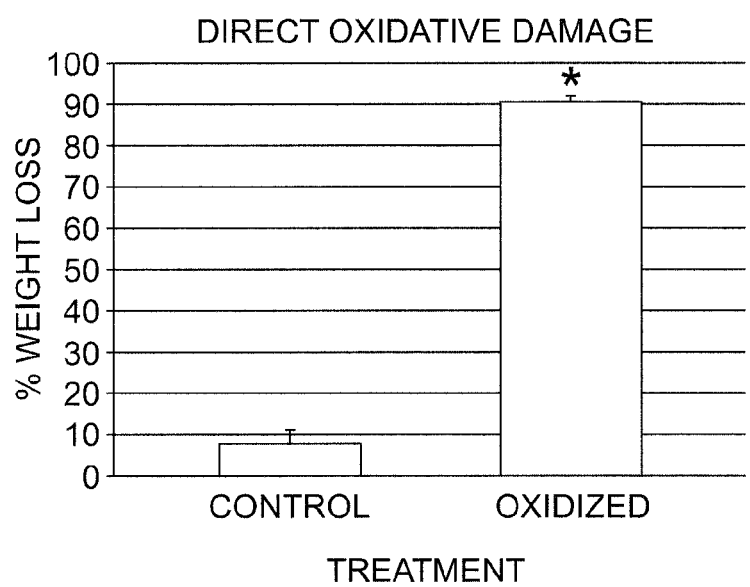
FIG. 1 shows wet weight loss in a glutaraldehyde pretreated bovine pericardium sample following peroxide incubation (Oxidized) as compared with a control sample (Control). An asterisk (*) means significant difference between the Control and Oxidized samples at $p<0.02$.

The present invention is based on the discovery that immobilizing an anti-oxidant or a combination of two or more antioxidants to a bioprosthetic heart valve leaflet tissue may reduce oxidative stress-based damage to the tissue. In one example, covalent attachment of an anti-oxidant, for example, 4-hydroxy-3,5-di-tert-butylphenylpropylamine hydrochloride (DBP-amine.HCl), to a bovine pericardium provided significant protection to the pericardium against oxidative damage.

Bioprosthetic Tissue

The present invention provides a bioprosthetic tissue incorporating an effective amount of an antioxidant to prevent oxidative degeneration of the bioprosthetic tissue in a subject, in which the antioxidant is covalently immobilized or attached to the bioprosthetic tissue.

A bioprosthetic tissue is a biological tissue obtained from an animal (e.g., a human) for use in a bioprosthesis, either in a fresh state or after being preserved from decay by, for example, chemical fixation or freezing. The bioprosthetic tissue may be a heterograft or a homograft. It may be a tissue obtained from any mammal (e.g., bovine, ovine, porcine and human tissues). Examples of the bioprosthetic tissue include heart, heart valve, pericardium, vascular graft, urinary tract, bladder component, tendon, bowel, and soft tissues. Preferably, the bioprosthetic tissue is a heart valve tissue. Any animal derived membranous material may be suitable for use, for example, equine pericardium, kangaroo pericardium, porcine pericardium, and bovine pericardium. Preferably, the bioprosthetic tissue is a porcine aortic valve or a bovine pericardium.

The bioprosthetic tissue may be fixed by any method suitable for subsequent implantation of the bioprosthetic tissue into a subject. Preferably, the fixed bioprosthetic tissue retains free groups for covalent attachment of an antioxidant. The free groups may be carboxylic groups, for example, from residues of aspartic and glutamic acids. The bioprosthetic tissue may be fixed chemically. Preferably, the bioprosthetic tissue is fixed with glutaraldehyde or epoxy-compounds (e.g., triglycidylamine). The bioprosthetic tissue may also be cryopreserved with liquid nitrogen.

Antioxidants

The antioxidant may be any molecule capable of inhibiting oxidation of other molecules, and suitable for covalent attachment to a bioprosthetic tissue. Techniques for covalent attachment of two molecules, including small molecules and/or biological molecules, are well known in the art. For example, chemical strategies used to attach phenolic antioxidants covalently to polyurethane to prevent polyurethane oxidative degradation may be adapted for covalent immobilization of the phenolic antioxidants to a bioprosthetic tissue.

The antioxidant may be derived from a natural antioxidant and modified for covalent attachment to a bioprosthetic tissue. Examples of natural antioxidants include glutathione, ascorbic acid (vitamin C), lipoic acid, uric acid, carotenes, α-tocopherol (vitamin E), ubiquinol (coenzyme Q) and melatonin.

The antioxidant may also be a synthetic antioxidant. Many commonly used antioxidants may be used, directly or with some modifications known in the art, for covalent attachment or immobilization to a bioprosthetic tissue. Antioxidants from any of several major classes may be employed. These include hindered amines (e.g., derivatives of 2,2,6,6-tetramethylpiperidine, Scheme 2, structure 4), aromatic amines (e.g., N,N'-disubstituted-p-phenylenediamines (e.g. Scheme 2 structure 1), alkylated diphenylamines (e.g., Scheme 2, structure 2), and derivatives of dihydroquinoline (e.g., Scheme 2, structure 3), high temperature stabilization agents such alpha-tocopherol, hydroxylamines (e.g., Scheme 2, structure 5), and lactones (e.g., benzofuranones, especially arylbenzofuranones such as in Scheme 2, structure 6 and Scheme 3, structure 8), and hindered phenols (e.g., 2,6-di-tert-butyl-p-cresol). Another useful class includes sulfur-based hydroperoxide decomposers known as thiosynergists, one example of which is shown in Scheme 3 as structure 7. Others are well known in the art. A thiosynergist may also be introduced by binding N-acetylcysteine by the thiol group to the bioprosthetic tissue, thereby forming a dialkyl sulfide. Suitable techniques for such binding are described, for example, by Fishbein et al., mentioned above.

Combinations of two or more antioxidants may also be used, including combinations from the same class and/or combinations employing antioxidants from different classes. Such combinations may result in longer antioxidant activity and/or synergy. For example, combinations of thiosynergists with antioxidants from other classes, for example hindered phenols, may afford pronounced synergistic action.

In some embodiments, the antioxidant is a phenol-based antioxidant. For example, the antioxidant may be 4-substituted 2,6-di-tert-butylphenol (DBP) or a derivative thereof. Preferably, the antioxidant is 4-hydroxy-3,5-di-tert-butylphenolpropylamine hydrochloride (DBP-amine.HCl). Covalent binding of the antioxidant molecule to the tissue should be performed in a way not compromising the effectiveness of the antioxidant action (for example, covalent immobilization of hindered phenols should not affect the phenolic OH, critical for the activity).

The subject is a mammal, for example, dog, cat, racehorse, bull, or human, in need of a bioprosthesis. Preferably, the subject is a human. The subject may be a female or male. The subject may be a child or an adult.

The subject may have suffered from a condition, disorder or disease, for example, the metabolic syndrome, hormonal deregulation, hypertension, extreme stress and weight loss. A subject having the metabolic syndrome is defined as set forth in the US National Cholesterol Education Program Adult Treatment Panel III (2001). (*JAMA*. 2002; 287(3): 356-359.PDF attached). The subject may have suffered from a renal disease or calcium/phosphorus imbalance. The subject may have suffered from increased reactive oxygen species (ROS). The subject may also have suffered from hyperglycemia-induced oxidative stress.

For each of the bioprosthetic tissues described herein, a preparation method is provided. The method comprises immobilizing covalently an effective amount of an antioxidant to the bioprosthetic tissue to prevent oxidative degeneration of the bioprosthetic tissue in a subject.

A bioprosthetic heart valve leaflet comprising a bioprosthetic tissue of the present invention is provided. The bioprosthetic tissue is treated with an effective amount of an antioxidant to prevent oxidative degeneration of the bioprosthetic tissue in a subject, and the antioxidant is covalently immobilized to the bioprosthetic tissue.

The present invention provides a method for preventing oxidative degeneration of a bioprosthetic tissue in a subject. The method comprises immobilizing covalently an effective amount of an antioxidant to the bioprosthetic tissue.

The term "preventing" as used herein means reducing or mitigating. Prevention may be assessed by quantitating a number of different parameters. Material studies such as described in the Examples can assess in vitro statistically significant differences in prevention of mass loss of weight due to oxidative stress, resistance to collagenase digestion—versus quantitation of increased susceptibility to this enzyme following oxidative stress. In vivo mitigation in an actual heart valve implant may be measured by cardiovascular testing such as echo-cardiograms, angiograms and computerized tomography, all of which may document improved bioprosthetic function over time due to prevention of oxidative stress. Thus, the reduction of oxidative degeneration of a bioprosthetic tissue may be measured by a conventional method, for example, reduced weight loss or an extension of functional life of the bioprosthetic tissue. Therefore, in animals, including human subjects, the extension of functional life of a bioprosthesis (e.g., a medical device) comprising the bioprosthetic tissue may be determined by quantitative testing such as ultrasound or x-ray/angiogram imaging. Microscopic or material analyses may be used to determine the success of the methods and compositions of this invention experimentally in retrieved in vivo specimens.

In the prevention method according to the present invention, the bioprosthetic tissue may be a heterograft or a homograft. It may be a tissue obtained from any mammal (e.g., bovine, ovine, porcine and human tissues). Examples of the bioprosthetic tissue include heart, heart valve, pericardium, vascular graft, urinary tract, bladder component, tendon, bowel, and soft tissues. Preferably, the bioprosthetic tissue is a heart valve tissue. More preferably, the bioprosthetic tissue a porcine aortic valve or a bovine pericardium.

In a prevention method according to the present invention, the bioprosthetic tissue may be fixed by any method suitable for subsequent implantation of the bioprosthetic tissue into a subject. Preferably, the fixed bioprosthetic tissue retains free groups for covalent attachment of an antioxidant or combination of antioxidants. The free groups may be carboxylic groups, for example, from residues of aspartic and glutamic acids in the tissue proteins. The bioprosthetic tissue may be fixed chemically. Preferably, the bioprosthetic tissue is fixed with glutaraldehyde or epoxy-compounds (e.g., triglycidylamine). The bioprosthetic tissue may also be cryopreserved with liquid nitrogen.

In a prevention method according to the present invention, the antioxidant may be any molecule capable of inhibiting oxidation of other molecules, and suitable for covalent attachment to a bioprosthetic tissue. Techniques for covalent attachment of two molecules, including small molecules and/or biological molecules, are well known in the art. For example, chemical strategies used to attach phenolic antioxidants covalently to polyurethane to prevent polyurethane oxidative degradation may be adapted for covalent immobilization of the phenolic antioxidants to a bioprosthetic tissue. The antioxidant may be derived from a natural antioxidant and modified for covalent attachment to a bioprosthetic tissue. Examples of natural antioxidants include glutathione, ascorbic acid (vitamin C), lipoic acid, uric acid, carotenes, α-tocopherol (vitamin E), ubiquinol (coenzyme Q) and melatonin.

The antioxidant may also be a synthetic antioxidant. Many commonly used antioxidants may be used, directly or with some modifications known in the art, for covalent attachment or immobilization to a bioprosthetic tissue. Antioxidants from any of several major classes may be employed. These include hindered amines (e.g., derivatives of 2,2,6,6-tetramethylpiperidine), aromatic amines (e.g., N,N'-disubstituted-p-phenylenediamine, alkylated diphenylamines, and derivatives of dihydroquinoline), high temperature stabilization agents such alpha-tocopherol, hydroxylamines (e.g., Scheme 2, structure 5), and lactones (e.g., benzofuranones, such as in Scheme 2, structure 6 and Scheme 3, structure 8), and hindered phenols (e.g., 2,6-di-tert-butyl-p-cresol). Another useful class includes sulfur-based hydroperoxide decomposers known as thiosynergists, one example of which is shown in Scheme 3 as structure 7. Others are well known in the art.

Combinations of two or more antioxidants may also be used, including combinations from the same class and/or combinations employing antioxidants from different classes. Such combinations may result in longer antioxidant activity and/or synergy. For example, combinations of thiosynergists with antioxidants from other classes, for example hindered phenols, may afford pronounced synergistic action.

In some embodiments, the antioxidant is a phenol-based antioxidant. For example, the antioxidant may be 4-substituted 2,6-di-tert-butylphenol (DBP) or a derivative thereof. Preferably, the antioxidant is 4-hydroxy-3,5-di-tert-butyl-phenolpropylamine hydrochloride (DBP-amine.HCl).

In a prevention method according to the present invention, the subject may be a mammal, for example, a pet (e.g., dogs and cats) or human. Preferably, the subject is a human. The subject may be a female or male. The subject may be a child or an adult. The subject may have suffered from a condition, disorder or disease, for example, the metabolic syndrome, hormonal deregulation, hypertension, extreme stress and weight loss. A subject having the metabolic syndrome is defined as set forth in the US National Cholesterol Education Program Adult Treatment Panel III (2001). The subject may have suffered from a renal disease or calcium/phosphorus imbalance. The subject may have suffered from increased reactive oxygen species (ROS). The subject may also have suffered from hyperglycemia-induced oxidative stress.

A composition for preparing a bioprosthetic tissue, fabricating a bioprosthetic heart valve leaflet comprising a bioprosthetic tissue, or preventing oxidative degeneration of a bioprosthetic tissue in a subject is provided. The compositions comprise an antioxidant or combination of two or more antioxidants capable of being covalently immobilized to the bioprosthetic tissue.

For a composition of the present invention, the bioprosthetic tissue may be a heterograft or a homograft. It may be a tissue obtained from any mammal (e.g., bovine, ovine, porcine and human tissues). Examples of the bioprosthetic tissue include heart, heart valve, pericardium, vascular graft, urinary tract, bladder component, tendon, bowel, and soft tissues. Preferably, the bioprosthetic tissue is a heart valve tissue. More preferably, the bioprosthetic tissue is a porcine aortic valve or a bovine pericardium.

For a composition of the present invention, the bioprosthetic tissue may be fixed by any method suitable for subsequent implantation of the bioprosthetic tissue into a subject. Preferably, the fixed bioprosthetic tissue retains free groups for covalent attachment of an antioxidant. The free groups may be carboxylic groups, for example, from residues of aspartic and glutamic acids. The bioprosthetic tissue may be fixed chemically. Preferably, the bioprosthetic tissue is fixed with glutaraldehyde or epoxy-compounds (e.g., triglycidylamine). The bioprosthetic tissue may also be cryopreserved with liquid nitrogen.

In a composition of the present invention, the antioxidant may be any molecule capable of inhibiting oxidation of other molecules, and suitable for covalent attachment to a bioprosthetic tissue. Techniques for covalent attachment of two or more molecules, including small molecules and/or biological molecules, are well known in the art. For example, chemical strategies used to attach phenolic antioxidants covalently to polyurethane to prevent polyurethane oxidative degradation may be adapted for covalent immobilization of the phenolic antioxidants to a bioprosthetic tissue. The antioxidant may be derived from a natural antioxidant and modified for covalent attachment to a bioprosthetic tissue. Examples of natural antioxidants include glutathione, ascorbic acid (vitamin C), lipoic acid, uric acid, carotenes, α-tocopherol (vitamin E), ubiquinol (coenzyme Q) and melatonin.

The antioxidant may also be a synthetic antioxidant. Many commonly used antioxidants may be used, directly or with some modifications known in the art, for covalent attachment or immobilization to a bioprosthetic tissue. Antioxidants from any of several major classes may be employed. These include hindered amines (e.g., derivatives of 2,2,6,6-tetramethylpiperidine), aromatic amines (e.g., N,N'-disubstituted-p-phenylenediamine, alkylated diphenylamines, and derivatives of dihydroquinoline), high temperature stabilization agents such alpha-tocopherol, hydroxylamines (e.g., Scheme 2, structure 5), and lactones (e.g., benzofuranones, such as in Scheme 2, structure 6 and Scheme 3, structure 8), and hindered phenols (e.g., 2,6-di-tert-butyl-p-cresol). Another useful class includes sulfur-based hydroperoxide decomposers known as thiosynergists, one example of which is shown in Scheme 3 as structure 7. Others are well known in the art.

Combinations of two or more antioxidants may also be used, including combinations from the same class and/or combinations employing antioxidants from different classes. Such combinations may result in longer antioxidant activity and/or synergy. For example, combinations of thiosynergists with antioxidants from other classes, for example hindered phenols, may afford pronounced synergistic action.

In some embodiments, the antioxidant is a phenol-based antioxidant. For example, the antioxidant may be 4-substituted 2,6-di-tert-butylphenol (DBP) or a derivative thereof. Preferably, the antioxidant is 4-hydroxy-3,5-di-tert-butyl-phenolpropylamine hydrochloride (DBP-amine.HCl).

For a composition of the present invention, the subject may be a mammal, for example, a pet (e.g., dogs and cats) or human. Preferably, the subject is a human. The subject may be a female or male. The subject may be a child or an adult. The subject may have suffered from a condition, disorder or disease, for example, the metabolic syndrome, hormonal deregulation, hypertension, extreme stress and weight loss. A subject having the metabolic syndrome is defined as set forth in the US National Cholesterol Education Program Adult Treatment Panel III (2001). The subject may have suffered from a renal disease or calcium/phosphorus imbalance. The subject may have suffered from increased reactive oxygen species (ROS). The subject may also have suffered from hyperglycemia-induced oxidative stress.

Tissue-Reactive Antioxidant Constructs

Antioxidant constructs capable of covalently binding to the bioprosthetic tissue can be considered to have the essential structure shown in Scheme 1, where A is an antioxidant, n is an integer from 1 to 10, L is a linker and X is a tissue-reactive functionality.

Scheme 1

$(A)_n$—L—X

In addition to hindered phenols, following are non-limiting examples of antioxidant functionalities (A) that may be tethered to the bioprosthetic tissue: (1) aromatic amines: N,N'-disubstituted-p-phenylenediamines (Scheme 2, 1), alkylated diphenylamines (Scheme 2, 2), derivatives of dihydroquinoline (Scheme 2, 3); (2) hindered amines, for example derivatives of 2,2,6,6-tetramethylpiperidine (Scheme 2, 4); (3) hydroxylamines (Scheme 2, 5), and (4) arylbenzofuranones (Scheme 2, 6).

Scheme 2

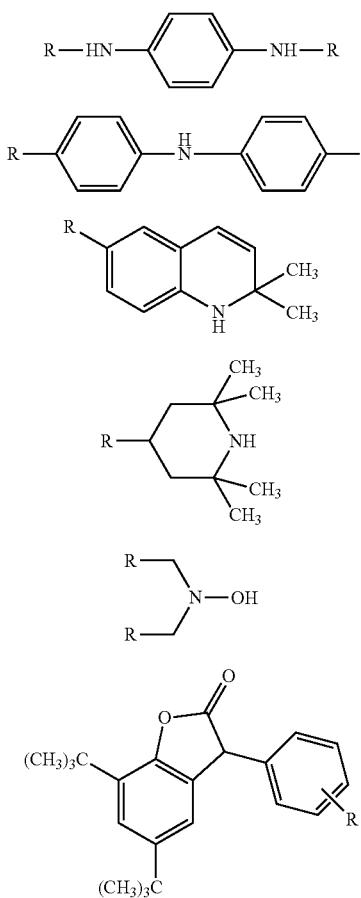

The linker L may contain one or more carbon atoms. It may also include carbonyls and heteroatoms (e.g., O, S, N and P) and arylene spacers. The linker should be attached to the antioxidant in a way not affecting the antioxidant action, preferably to a hydrocarbon radical R shown in Scheme 2. The tissue-reactive functionality X may for example be an amino group (e.g., for reaction with the residual carboxy groups of the tissue), a carboxy group (or its active ester, e.g., for reaction with the amino groups of the tissue), a photo-reactive group (e.g., aromatic azide, residue of benzophenone, and anthraquinone, which are capable of binding to the tissue under UV-irradiation), or any other group capable of participating in any known method of bioconjugation (e.g., chemistry of thiols and thiol-reactive groups, click chemistry, and Staudinger ligation).

Examples of suitable tissue-reactive antioxidant constructs are shown in Scheme 3.

Scheme 3

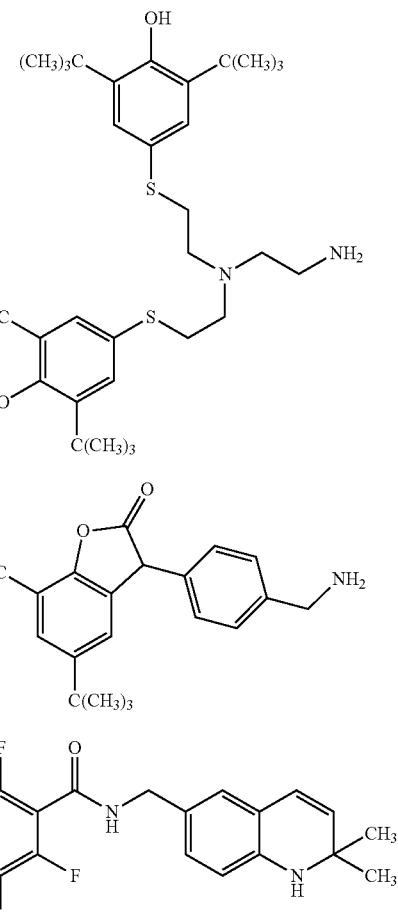

Tissue-reactive antioxidant construct 7 has two hindered phenolic antioxidant moieties, a linker containing heteroatoms S and N, and a tissue-reactive group of $NH_2$. The sulfur atoms in the linker serve also as synergists, enhancing the antioxidant action of the hindered phenolic moieties. Tissue-reactive antioxidant construct 8 is an example of a tissue-modifier containing an arylbenzofuranone antioxidant moiety. Constructs 7 and 8 may be covalently bonded to the tissue with the aid of a coupling agent (e.g., 1-(3-dimethylaminopropyl)-3-ethylcarbodiimide hydrochloride (EDC)), or other agents suitable for coupling of carboxy and amino groups (e.g., 1-cyclohexyl-3-morpholinoethylcarbodiimide metho p-toluene sulfonate (CMC), and benzotriazol-1-yloxy-tris-dimethylamino-phosphonium hexafluorophosphate). An intermediate-stabilizing agent (e.g., N-hydroxysuccinimide (SuOH), 1-hydroxy 7-azabenzotriazole (HOAt), pentafluorophenol, etc.) may additionally be used with certain coupling agents to increase efficacy by stabilizing the active intermediate, as known in the art. Other coupling agents, for example benzotriazol-1-yloxy-tris-dimethylamino-phosphonium hexafluorophosphate (BOP), do not require such stabilization.

Construct 9 contains a dihydroquinoline-type of antioxidant having a linker containing a carbonyl and a N-heteroatom, wherein the tissue-reactive group is a photo-activatable fluoroaromatic azide. Other techniques for photoactive coupling may also be used, for example as disclosed in U.S. Pat.

No. 7,635,734. In addition thiol based chemistry may be used, as well as affinity methods such as avidin-biotin etc. Suitable thiol-based chemistry is described for example in Fishbein, I., Alferiev, I., Bakay, M., Stachelek, S. J., Sobolewski, P., Lai, M., Choi, H., Chen, L W., and Levy, R. J., *Local delivery of gene vectors from bare-metal stents by use of a biodegradable synthetic complex inhibits in-stent restenosis in rat carotid arteries*, Circulation (2008) 117, 2096-2103, and is based on well known chemical methodologies. Suitable coupling using avidin-biotin affinity is described for example in Wilchek, M., and Bayer, E. A., *Introduction to avidin-biotin technology*, Methods Enzymol (1990) 184, 5-13. The methods of the invention may further comprise similarly tethering another type of agent, for example an agent suitable for preventing calcification, to the tissue.

Exemplary Embodiments of the Invention

In some embodiments, the invention provides a bioprosthetic tissue treated with an effective amount of an antioxidant or combination of antioxidants to prevent oxidative degeneration of the bioprosthetic tissue in a subject, wherein the antioxidant is covalently immobilized to the bioprosthetic tissue.

In some embodiments, the bioprosthetic tissue is a heterograft.

In some embodiments, the bioprosthetic tissue is a homograft.

In some embodiments, the bioprosthetic tissue is a tissue selected from the group consisting of bovine, ovine, porcine, equine, other non-human vertebrate tissues and human tissues.

In some embodiments, the bioprosthetic tissue is a tissue selected from the group consisting of heart, heart valve, pericardium, vascular graft, urinary tract, bladder component, tendon, bowel, and soft tissues.

In some embodiments, the bioprosthetic tissue is a heart valve tissue.

In some embodiments, the bioprosthetic tissue is a porcine aortic valve.

In some embodiments, the bioprosthetic tissue is a bovine pericardium.

In some embodiments, the bioprosthetic tissue is fixed with glutaraldehyde.

In some embodiments, the bioprosthetic tissue is preserved with liquid nitrogen.

In some embodiments, the bioprosthetic tissue is one in which the antioxidant is derived from a natural antioxidant selected from the group consisting of glutathione, ascorbic acid (vitamin C), lipoic acid, uric acid, carotenes, α-tocopherol (vitamin E), ubiquinol (coenzyme Q) and melatonin.

In some embodiments, the bioprosthetic tissue is one in which the antioxidant is a synthetic antioxidant.

In some embodiments, the bioprosthetic tissue is one in which the antioxidant is a phenol-based antioxidant.

In some embodiments, the bioprosthetic tissue is one in which the antioxidant is 4-substituted 2,6-di-tert-butylphenol (DBP) or a derivative thereof.

In some embodiments, the bioprosthetic tissue is one in which the antioxidant is 4-hydroxy-3,5-di-tert-butylphenol-propylamine hydrochloride (DBP-amine.HCl).

In some embodiments, the bioprosthetic tissue is one in which the antioxidant comprises a hindered phenol and at least one additional antioxidant selected from the group consisting of aromatic amines, alkylated diphenylamines, derivatives of dihydroquinoline, hindered amines, hydroxylamines and arylbenzofuranones.

In some embodiments, the bioprosthetic tissue is one in which the antioxidant comprises a hindered phenol and a thiosynergist.

In some embodiments, the bioprosthetic tissue is one in which the antioxidant comprises a compound according to structure 7

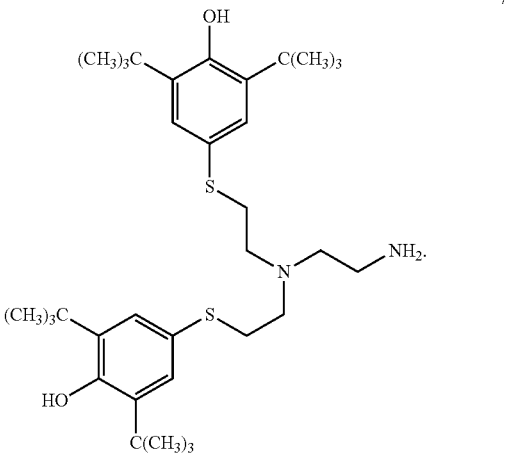

7

In some embodiments, the bioprosthetic tissue is one in which the antioxidant comprises a compound according to structure 8

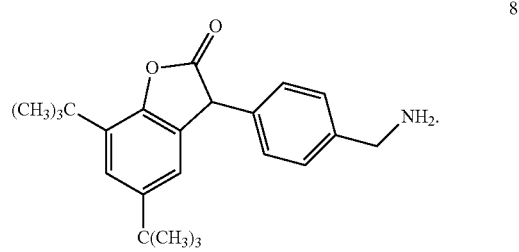 [SMILES: CC(C)(C)c1cc2c(c(C(C)(C)C)c1)OC(=O)C2c1ccc(CN)cc1]

8

In some embodiments, the bioprosthetic tissue is one in which the antioxidant comprises a compound according to structure 9

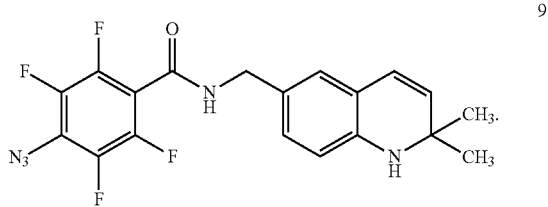 [SMILES: CC1(C)C=Cc2cc(CNC(=O)c3c(F)c(F)c(N=[N+]=[N-])c(F)c3F)ccc2N1]

9

In some embodiments, the bioprosthetic tissue is a heart valve leaflet.

The invention provides a method for preparing a bioprosthetic tissue according to any of the aforementioned embodiments, comprising immobilizing the antioxidant to the bioprosthetic tissue.

The invention provides a method for treating a subject in need of a bioprosthetic tissue, comprising treating the subject with the bioprosthetic tissue according to any of the aforementioned embodiments.

In some embodiments, the method of treating a subject is one in which the subject is a human.

In some embodiments, the method of treating a subject is one in which the subject is a female.

In some embodiments, the method of treating a subject is one in which the subject is a male.

In some embodiments, the method of treating a subject is one in which the subject has suffered from the metabolic syndrome, hormonal deregulation, hypertension, extreme stress or weight loss.

In some embodiments, the method of treating a subject is one in which the subject has suffered from increased reactive oxygen species (ROS).

In some embodiments, the method of treating a subject is one in which the subject has suffered from hyperglycemia-induced oxidative stress.

The invention also provides a compound according to structure 7

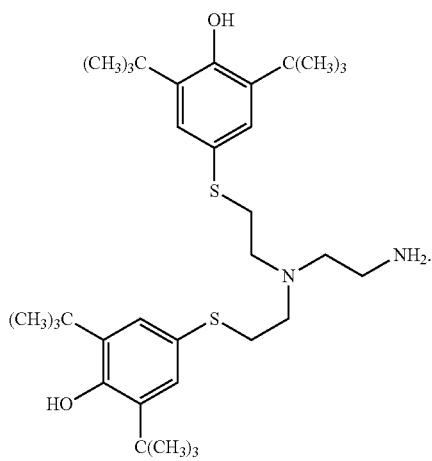

The invention also provides a compound according to structure 8

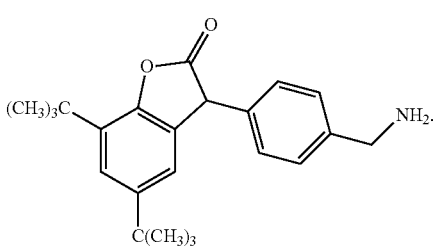

The invention also provides a compound according to structure 9

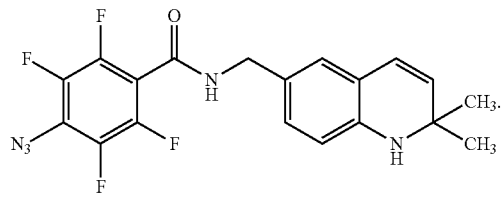

EXAMPLES

Example 1. Oxidative Stress in Bioprosthetic Heart Valve Deterioration

In vitro model system studies were carried out using a modification of a well established oxidative stress system involving incubating synthetic polymers in hydrogen peroxide solutions (Stachelek S J, et al. *J Biomed Mater Res A* 2006; 78:653-61). This experimental system was originally developed and validated for investigating polyurethane oxidative degradation, and was adapted for studies of oxidative stress in bioprosthetic heart valve leaflet samples.

Figure 2:
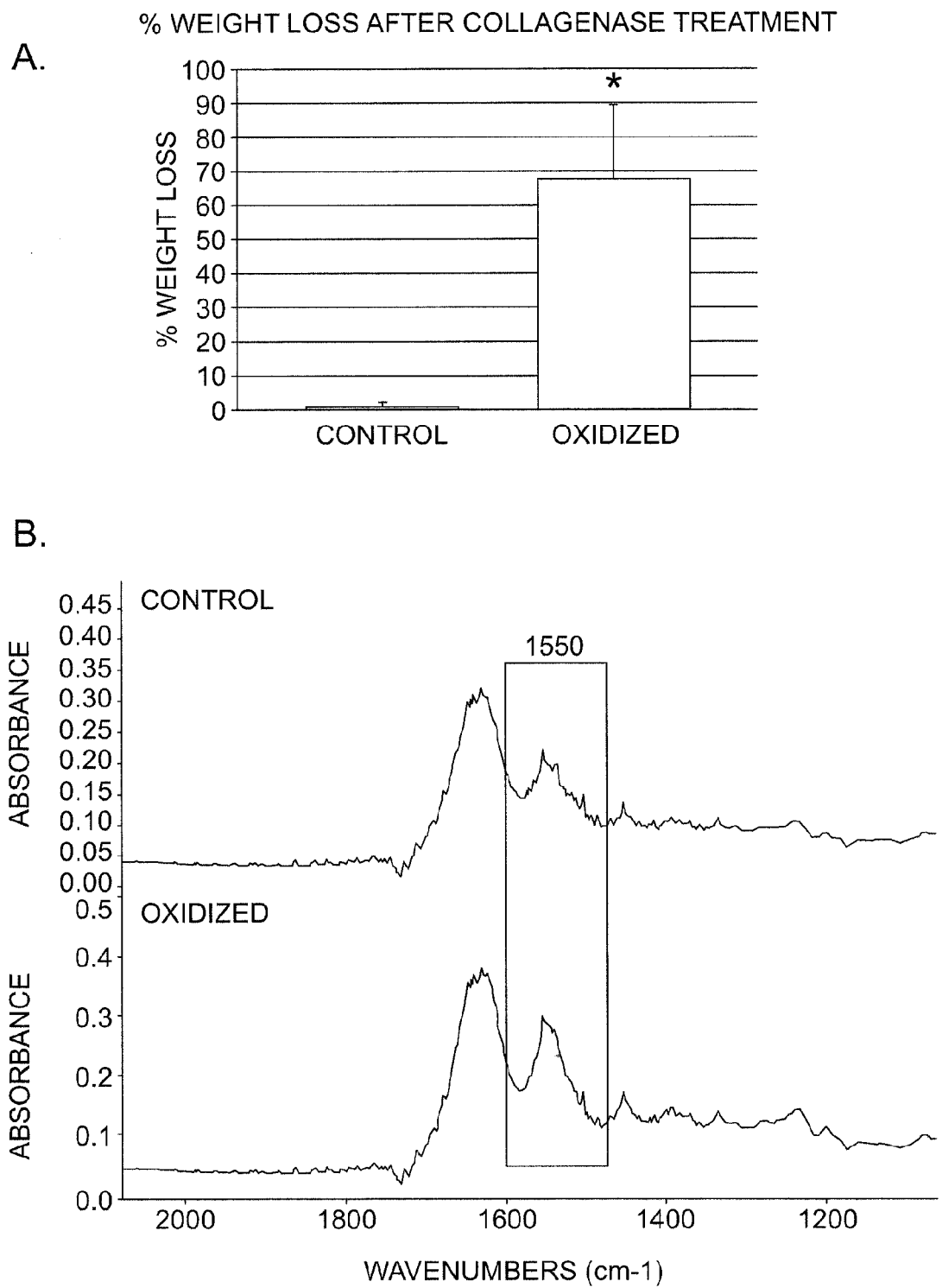
FIG. 2 shows (A) dry weight loss in a glutaraldehyde pretreated bovine pericardium sample following collagenase treatment on the remaining residual material after peroxide incubation (Oxidized) as compared with a control sample (Control), and (B) Fourier transform infrared (FTIR) spectroscopy of glutaraldehyde fixed bovine pericardium before (Control) and after oxidation (Oxidized) demonstrating an increased peak at 1550 $cm^{-1}$. An asterisk (*) in FIG. 2(A) means significant difference between the Control and Oxidized samples at $p<0.02$.

In brief, bovine pericardium was fixed in 0.6% glutaraldehyde using established conditions for preparing this material for use in bioprosthetic heart valves. These glutaraldehyde cross-linked bovine pericardium samples (typically 1 cm×1 cm) were incubated in 20% $H_2O_2$ for 14 days at 37° C. Solutions were changed every three days. At the end of the incubation period, the samples were washed with water or PBS, and stored at 4° C. until later analysis. Samples designated as controls were incubated in water only. The wet weight of each sample was recorded prior to the start of the incubation, and after the wash steps at the end of the study. The percent weight loss from the original wet weight is presented in FIG. 1 as a direct index of oxidative damage. The control and oxidized samples from the in vitro model of oxidative degradation were lyophilized for 48 hours. The dry weight of each sample was recorded prior to treatment with collagenase. Samples were digested for 24 hours at 37° C. in a solution containing 600 units/ml collagenase from *Clostridium histolyticum* (Sigma 9001-12-1), phosphate buffered saline and 0.1% bovine serum albumin. Following digestion, samples were pelleted by centrifugation at 10,000 rpm at 4° C. Sample were washed with saline and lyophilized for 48 hours. The weight of each sample was recorded after the lyophilization period. Data were reported as a percent weight loss from the original dry weight and is presented in FIG. 2A as % weight loss after collagenase treatment (P<0.001). As indicated, oxidative stress due to hydrogen peroxide exposure causes substantial material loss (FIG. 1). In addition, the material remaining after peroxide exposure is significantly more susceptible to collagenase digestion (FIG. 2A). Thus, glutaraldehyde pretreated bovine pericardium is strongly affected by oxidative stress with primary material degradation and increased susceptibility to enzymatic digestion. In addition, oxidation gave rise to an increased 1550 $cm^{-1}$ peak per FTIR (FIG. 2B) that is likely due oxidation reaction products.

Prior in vivo model studies have established that bioprosthetic heart valve leaflet calcification occurs in either rat subdermal implants or sheep mitral valve replacements, which display a pathology that is comparable to calcific failure of human implants of bioprosthetic heart valves (Schoen and Levy, *Ann Thorac Surg* 2005; 79:1072-80). In the studies shown below, an immunostaining marker for ROS, nitrotyrosine, was used to demonstrate the strong presence of ROS, per nitrotyrosine positive staining in calcified bioprosthetic heart valve leaflets retrieved from rat subdermal implants and sheep mitral valve replacements. The presence of nitrotyrosine indicates that nitric oxide-peroxynitrite oxidative stress has modified the proteins of these heart valve leaflets. Since calcification was also present in the positively staining retrievals, the results imply that oxidative stress can occur in the presence of calcification, and may even contribute to the calcification mechanism.

Figure 3:
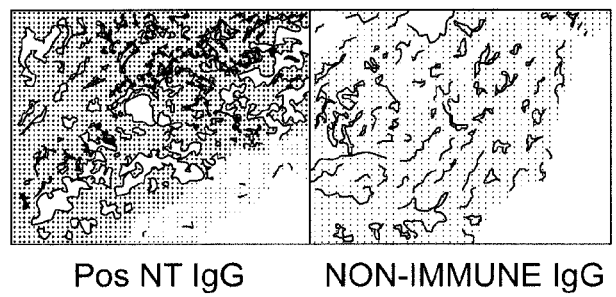
FIG. 3 shows nitrotyrosine immunostaining on (A) glutaraldehyde-pretreated and calcified 90-day rat subdermal explants, (B) glutaraldehyde-ethanol-pretreated and non-calcified 90-day rat subdermal explants, and (C) calcified 59-day sheep mitral valve explants, using rabbit anti-nitrotyrosine IgG (left panels) or nonspecific rabbit IgG (right panels) at the same concentration of 5 µg/ml.
Figure 3:
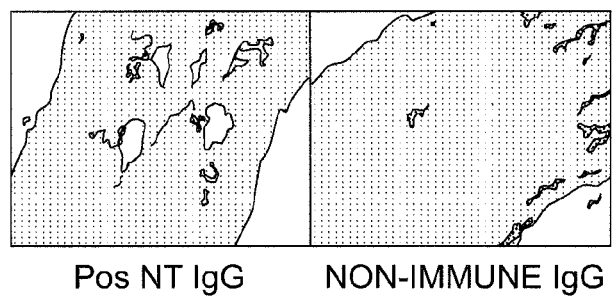
Figure 3:
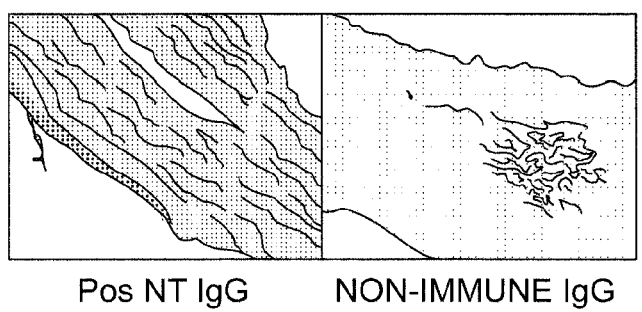

Nitrotyrosine immunostaining was carried out on formalin-fixed explants from either 90-day rat subdermal experiments (FIG. 3A: glutaraldehyde-pretreated and calcified, or FIG. 3B: glutaraldehyde-EtOH-pretreated and non-calcified) or from a sheep mitral valve replacement (FIG. 3C: 59 days duration and calcified). Sections of 12 μm thickness cut from formalin-fixed explants were stained either using rabbit anti-nitrotyrosine (provided by Dr. H. Ischiropoulos; The Children's Hospital of Philadelphia), or as a negative control, nonspecific rabbit IgG, in both cases at an immunoglobulin concentration of 5 μg/ml. Sections were blocked for non-specific peroxidase and reaction with secondary antibody (biotinylated goat anti-rabbit) before color development, sequentially using a VectaStain ABC kit and ImmPACT DAB chromogen (Vector Labs, Inc, Burlingame, Calif.) per standard procedures well known in the art. Positive staining is indicated by intense red-brown color, which is absent in non-calcified rat subdermal implants or when non-immune IgG was used. Representative results are shown indicating the presence of strong nitrotyrosine staining co-incident with calcification. Additional negative control studies included anti-nitrotyrosine which was pre-absorbed with blocking peptide (gift of Dr. H Ischiropoulos); this demonstrated the specificity of positive sample stains for nitrotyrosine. Thus, these in vivo results demonstrate the presence of oxidative stress in calcified explants from both rat subdermal studies and sheep circulatory explants. Nitrotyrosine is a specific by-product of oxidative stress, in which peroxynitrite reacts with protein-based tyrosine residues. Thus, it can be seen that oxidative stress was clearly present in calcifying bioprosthetic heart valves.

Example 2. Prevention of Oxidative Stress-Induced Damage in Bioprosthetic Heart Valve Leaflets In these studies, it was investigated whether the use of an anti-oxidant could prevent the extensive breakdown of bioprosthetic leaflets due to ROS. A local therapy strategy was investigated involving the covalent attachment of an anti-oxidant compound to bioprosthetic leaflets that were already crosslinked with glutaraldehyde.

A chemical immobilization strategy was adopted to improve the oxidative stability of a bioprosthetic tissue via covalent attachment of antioxidant functions based on hindered phenolic residues covalently immobilized on collagenous biomaterials. The modification employed direct coupling of the collagen's carboxylic groups (from residues of aspartic and glutamic acids) with the amine groups of a hindered phenolic antioxidant using water-soluble 1-(3-dimethylaminopropyl)-3-ethylcarbodiimide hydrochloride (EDC). Among many possibilities, 4-hydroxy-3,5-di-tert-butylphenylpropylamine hydrochloride (DBP-amine.HCl) was used as a suitable antioxidant possessing an amino group, which is water-soluble and can be used in aqueous media (preparation described in Dyubchenko et al., *Pharm. Chem. J.* 2006, 40(5), 243-247, translated from *Khimiko-Farmatsevticheskii Zhurnal* 2006, 40(5), 10-13). To capture the unstable intermediate formed in the reaction of carboxylic groups with EDC, N-hydroxysuccinimide (SuOH) was added into the reaction mixture. As a result, more stable amine-reactive Su-esters were formed, and the antioxidant was then bound to the tissue via stable amide bonds, as shown in Scheme 4.

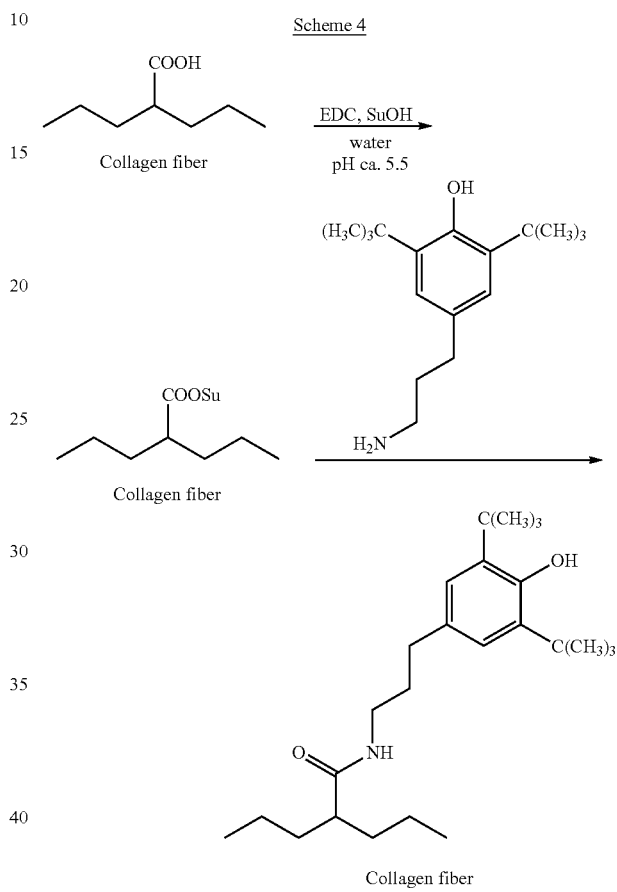

Figure 4:
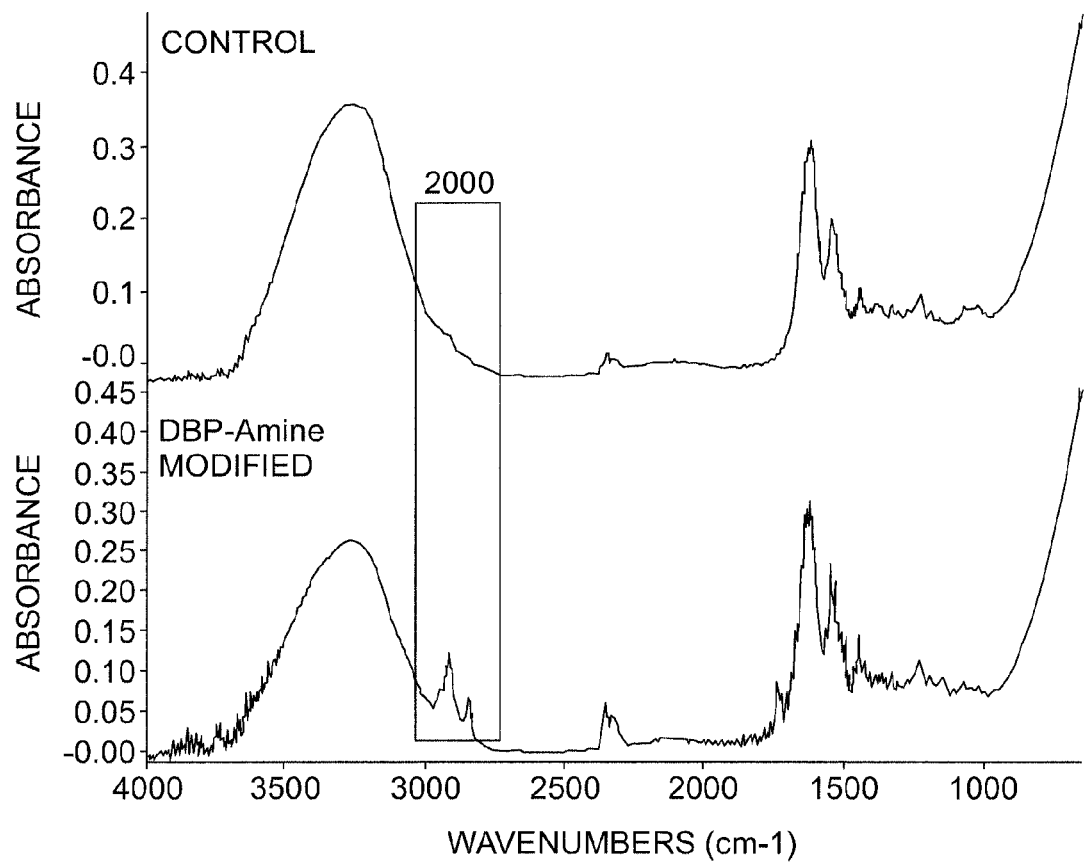
FIG. 4 shows Fourier transform infrared (FTIR) spectroscopy of glutaraldehyde fixed bovine pericardium samples before (Control) and after the covalent attachment of DBP (DBP-Amine Modified) demonstrating novel peaks at 2900 $cm^{-1}$.

Thus, to carry out these reactions a solution was prepared from water (9.5 ml), 4-hydroxy-3,5-di-tert-butylphenylpropylamine hydrochloride (DBP-amine.HCl, 110 mg) and N-hydroxysuccinimide (SuOH, 50 mg). To accelerate the dissolution of DBP-amine.HCl, the mixture may be warmed to ca. 40-50° C., but should be cooled before the addition of SuOH. The solution was adjusted to pH ca. 5.5 with 0.05 M aqueous $KHCO_3$ solution, and 1-ethyl-3-(3-dimethylaminopropyl)carbodiimide hydrochloride (EDC, 0.12 g) was added immediately before use. The tissue was allowed to react in the above solution for 24-36 h at room temperature with gentle stirring. Finally, the tissue was thoroughly rinsed with copious amounts of water. After rinsing with water, the tissue could be repeatedly incubated as above with a fresh portion of the solution, if necessary. FTIR analyses (FIG. 4) demonstrated the presence of two novel peaks at ca. 2900 $cm^{-1}$, suggesting the covalent attachment of DBP.

Figure 5:
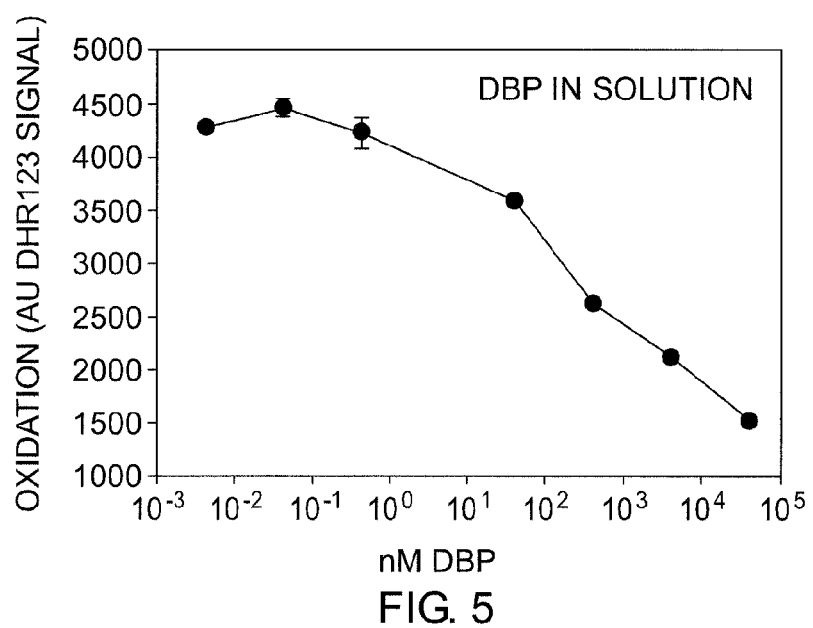
FIG. 5 shows reduction of oxidation signal caused by increasing concentrations of DBP in solution.
Figure 6:
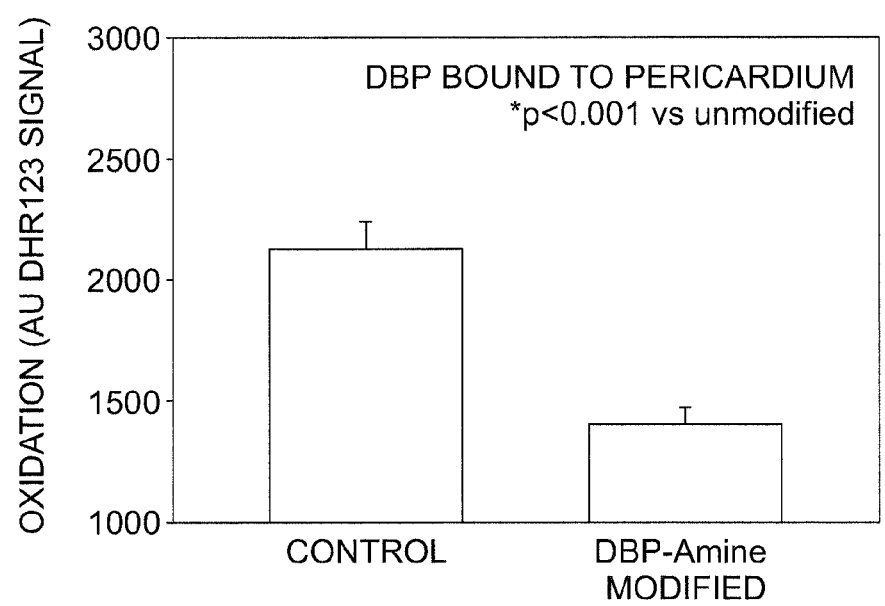
FIG. 6 shows oxidation signals obtained from glutaraldehyde fixed bovine pericardium samples before (Control) and after the covalent attachment of DBP (DBP-Amine Modified). An asterisk (*) means significant difference between the Control and DBP-Amine Modified samples at $p<0.02$.

The ability of DBP to inhibit ROS activity was verified both in solution and when bound to glut-pretreated pericardium, as described above, by monitoring the fluorescence of dihydrorhodamine-123 (DHR123; Molecular Probes Inc., Eugene Oreg.), which is a commonly used measure of oxidation due to ROS. Briefly, the capacity of DBP to reduce ROS activity was proven in this system by titrating DBP in solution against the oxidant hydrogen peroxide ($H_2O_2$) in the presence of DHR123. This resulted in a dose-dependent inhibition of oxidation signal (FIG. 5). Under the same conditions, samples of pericardium to which DBP had been covalently attached likewise reduced oxidation (FIG. 6).

Figure 7:
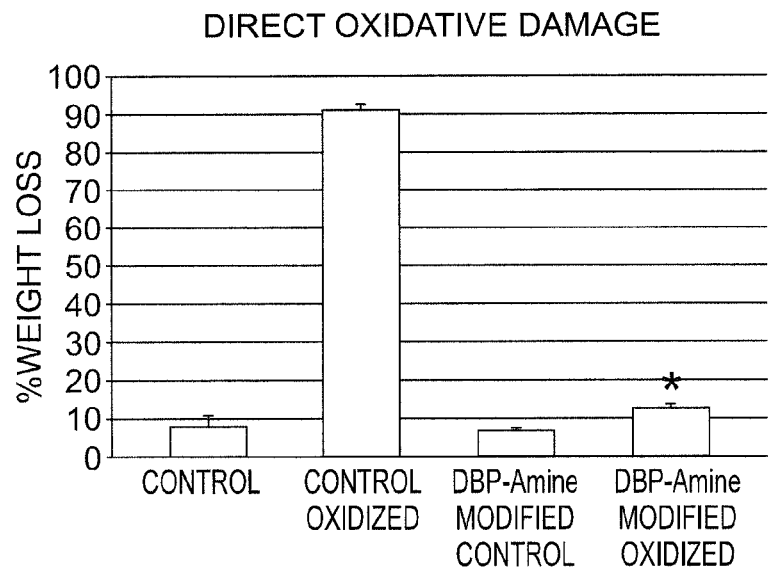
FIG. 7 shows wet weight loss due to direct oxidative damage in glutaraldehyde fixed bovine pericardium samples before (Control) and after the covalent attachment of DBP (DBP-Amine Modified), either following peroxide incubation (Oxidized) or not. An asterisk (*) means significant difference between the Control and DBP-Amine Modified samples at $p<0.02$.
Figure 8:
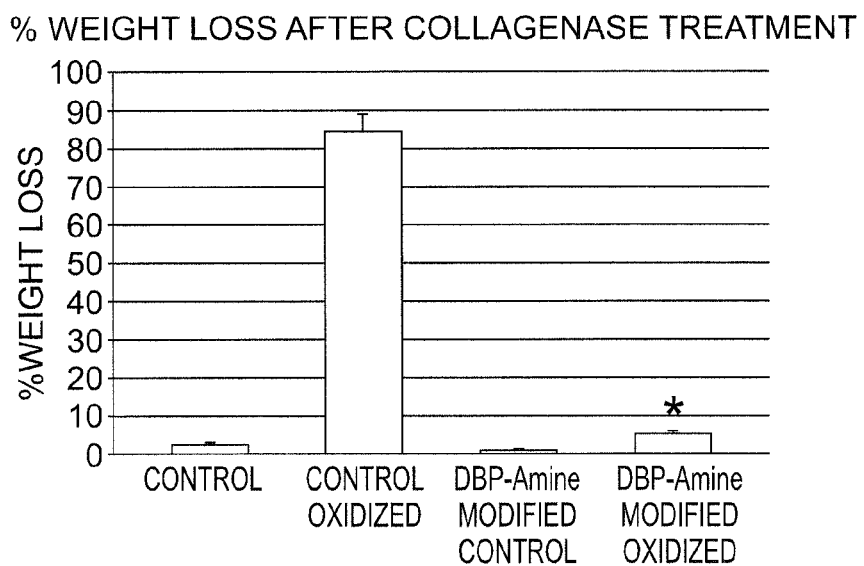
FIG. 8 shows dry weight loss in glutaraldehyde pretreated bovine pericardium samples before (Control) and after the covalent attachment of DBP (DBP-Amine Modified) after collagenase treatment of the remaining residual material following peroxide incubation (Oxidized) or not. An asterisk (*) means significant difference between the Control and DBP-Amine Modified samples at $p<0.02$.

DBP-modified glutaraldehyde-fixed bovine pericardium was investigated in the same hydrogen peroxide system described above (FIGS. 1 and 2) to assess ROS-damage to this biomaterial. Accordingly, FIG. 7 shows weight loss due to direct oxidative damage, and FIG. 8 shows weight loss after subsequent collagenase digestion. Both indicate a significant (P*<0.001) protective effect of DBP modification against oxidative damage, re. weight loss and subsequent collagenase digestibility (FIGS. 7 and 8).

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A bioprosthetic tissue treated with an effective amount of an antioxidant or combination of antioxidants to prevent oxidative degeneration of the bioprosthetic tissue in a subject, wherein the antioxidant is covalently immobilized to the bioprosthetic tissue, and wherein the antioxidant comprises a compound represented by formula (7):

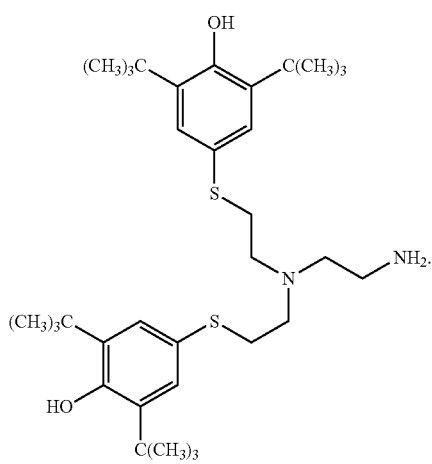

7

2. The bioprosthetic tissue of claim 1, wherein the bioprosthetic tissue is a heterograft.
3. The bioprosthetic tissue of claim 1, wherein the bioprosthetic tissue is a homograft.
4. The bioprosthetic tissue of claim 1, wherein the bioprosthetic tissue is a tissue selected from the group consisting of bovine, ovine, porcine, equine, other non-human vertebrate tissues and human tissues.
5. The bioprosthetic tissue of claim 1, wherein the bioprosthetic tissue is a tissue selected from the group consisting of heart, heart valve, pericardium, vascular graft, urinary tract, bladder component, tendon, bowel, and soft tissues.
6. The bioprosthetic tissue of claim 1, wherein the bioprosthetic tissue is a heart valve tissue.
7. The bioprosthetic tissue of claim 1, wherein the bioprosthetic tissue is a porcine aortic valve.
8. The bioprosthetic tissue of claim 1, wherein the bioprosthetic tissue is a bovine pericardium.
9. The bioprosthetic tissue of claim 1, wherein the bioprosthetic tissue is fixed with glutaraldehyde.
10. The bioprosthetic tissue of claim 1, wherein the bioprosthetic tissue is preserved with liquid nitrogen.
11. The bioprosthetic tissue of claim 1, wherein the antioxidant further comprises an antioxidant derived from a natural antioxidant selected from the group consisting of glutathione, ascorbic acid (vitamin C), lipoic acid, uric acid, carotenes, α-tocopherol (vitamin E), ubiquinol (coenzyme Q) and melatonin.
12. The bioprosthetic tissue of claim 1, wherein the antioxidant further comprises a synthetic antioxidant.
13. The bioprosthetic tissue of claim 12, wherein the antioxidant further comprises a phenol-based antioxidant.
14. The bioprosthetic tissue of claim 1, wherein the antioxidant further comprises 4-substituted 2,6-di-tert-butylphenol (DBP) or a derivative thereof.
15. The bioprosthetic tissue of claim 1, wherein the antioxidant further comprises 4-hydroxy-3,5-di-tert-butylphenolpropylamine hydrochloride (DBP-amine.HCl).
16. The bioprosthetic tissue of claim 1, wherein the antioxidant further comprises a hindered phenol and at least one additional antioxidant selected from the group consisting of aromatic amines, alkylated diphenylamines, derivatives of dihydroquinoline, hindered amines, hydroxylamines and arylbenzofuranones.
17. The bioprosthetic tissue of claim 1, wherein the antioxidant further comprises a hindered phenol.
18. The bioprosthetic tissue of claim 1, wherein the antioxidant further comprises a compound represented by formula (8):

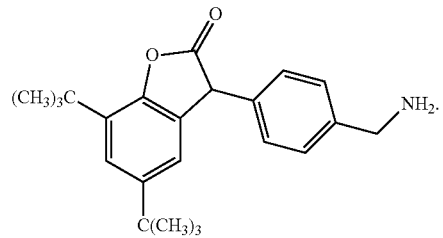

8

19. The bioprosthetic tissue of claim 1, wherein the antioxidant further comprises a compound represented by formula (9):

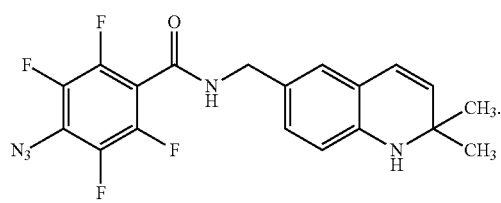

9

20. The bioprosthetic tissue of claim 1, wherein the bioprosthetic tissue is a heart valve leaflet.
21. A method for preparing a bioprosthetic tissue according to claim 1, comprising immobilizing the antioxidant to the bioprosthetic tissue.

22. A method for treating a subject in need of a bioprosthetic tissue, comprising treating the subject with the bioprosthetic tissue of claim 1.

23. The method of claim 22, wherein the subject is a human.

24. The method of claim 22, wherein the subject is a female.

25. The method of claim 22, wherein the subject is a male.

26. The method of claim 22, wherein the subject has suffered from the metabolic syndrome, hormonal deregulation, hypertension, extreme stress or weight loss.

27. The method of claim 22, wherein the subject has suffered from increased reactive oxygen species (ROS).

28. The method of claim 22, wherein the subject has suffered from hyperglycemia-induced oxidative stress.

* * * * *